United States Patent
Ah et al.

(10) Patent No.: US 8,628,650 B2
(45) Date of Patent: Jan. 14, 2014

(54) METHOD AND APPARATUS FOR MEASURING ISOELECTRIC POINT USING FIELD EFFECT TRANSISTOR

(75) Inventors: Chil Seong Ah, Daejeon (KR); Ansoon Kim, Daejeon (KR); Chan Woo Park, Daejeon (KR); Chang-Geun Ahn, Daejeon (KR); Jong-Heon Yang, Daejeon (KR); In Bok Baek, Cheongju-si (KR); Taeyoub Kim, Seoul (KR); Gun Yong Sung, Daejeon (KR); Seon-Hee Park, Daejeon (KR); Han Young Yu, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 258 days.

(21) Appl. No.: 13/058,120

(22) PCT Filed: Dec. 16, 2008

(86) PCT No.: PCT/KR2008/007452
§ 371 (c)(1),
(2), (4) Date: Feb. 8, 2011

(87) PCT Pub. No.: WO2010/016643
PCT Pub. Date: Feb. 11, 2010

(65) Prior Publication Data
US 2011/0139637 A1    Jun. 16, 2011

(30) Foreign Application Priority Data
Aug. 8, 2008 (KR) ............ 10-2008-0077893

(51) Int. Cl.
*B03C 5/02* (2006.01)
(52) U.S. Cl.
USPC ............ 204/459; 204/548; 204/610; 204/644

(58) Field of Classification Search
USPC ................ 204/450–470, 546–550, 600–621, 204/641–645
See application file for complete search history.

(56) References Cited

U.S. PATENT DOCUMENTS

| 4,238,757 | A | 12/1980 | Schenck |
| 7,839,134 | B2 * | 11/2010 | Lee et al. ............ 324/71.1 |
| 2007/0231211 | A1 * | 10/2007 | Yoo et al. ............ 422/88 |

FOREIGN PATENT DOCUMENTS

KR    10-0732610    6/2007

(Continued)

OTHER PUBLICATIONS

Cui, Yi et al., "Nanowire Nanosensors for Highly Sensitive and Selective Detection of Biological and Chemical Species," Science, vol. 293:1289-1292 (2001).

(Continued)

*Primary Examiner* — Bach Dinh
(74) *Attorney, Agent, or Firm* — Nelson Mullins Riley & Scarborough LLP; Anthony A. Laurentano, Esq.

(57) ABSTRACT

Provided are a method and apparatus for measuring an isoelectric point using a field effect transistor. The method includes providing a field effect transistor including a substrate, source and drain electrodes disposed on the substrate and spaced apart from each other, and a channel region between the source and drain electrodes, providing a first electrolyte solution having a first concentration to the channel region of the field effect transistor and measuring a first current value of the channel region between the source and drain electrodes, providing a second electrolyte solution having a second concentration greater than the first concentration and measuring a second current value of the channel region between the source and drain electrodes, and determining the isoelectric point of the field effect transistor or a material disposed on the field effect transistor using a difference between the first and second current values.

20 Claims, 5 Drawing Sheets

(56) References Cited

FOREIGN PATENT DOCUMENTS

| KR | 10-0738081 | 7/2007 |
| KR | 10-0773548 | 11/2007 |
| KR | 10-0773549 | 11/2007 |

OTHER PUBLICATIONS

Stern, Eric et al., "Importance of the Debye Screening Length of Nanowire Field Effect Transistor Sensors," Nano Letters, vol. 7(11):3405-3409 (2007).
International Search Report and Written Opinion for Application No. PCT/KR2008/007452, dated Mar. 11, 2009.

* cited by examiner

METHOD AND APPARATUS FOR MEASURING ISOELECTRIC POINT USING FIELD EFFECT TRANSISTOR

RELATED APPLICATIONS

This application is a 35 U.S.C. §371 national stage filing of PCT Application No. PCT/KR2008/007452 filed on Dec. 16, 2008, which claims priority to, and the benefit of, Korean Patent Application No. 10-2008-0077893 filed on Aug. 8, 2008. The contents of the aforementioned applications are hereby incorporated by reference.

TECHNICAL FIELD

The present invention disclosed herein relates to a method and apparatus for measuring an isoelectric point (pI). More particularly, the present invention relates to a method and apparatus for accurately measuring an isoelectric point of a bio molecule or material using a field effect transistor (FET).

The present invention has been derived from a research undertaken as a part of the information technology (IT) development business by Ministry of Information and Communication and Institute for Information Technology Advancement, Republic of Korea (Project management No.: 2006-S-007-03, Project title: Module System for Ubiquitous Health Care).

BACKGROUND ART

Bio molecules such as proteins very vary in size and shape and thus there are thousands to tens of thousands of kinds of proteins in accordance with the sizes and shapes.

The protein is a polymer in which many kinds of amino acids are arranged. The amino acids include an amino group (—$NH_2$) and a carboxyl group (—COOH). That is, one protein molecule is formed of many kinds of amino acids and thus has a zwitterions characteristic having not only cations but also anions. A property of the protein varies depending on an amount of net charges generated by coupling and separation of proton ions (H+).

There is a point where a sum of total charges becomes 0 in a bio molecule having many cations and anions. This point is referred to as an isoelectric point (pI). That is, the isoelectric point indicates a pH value in case where a net charge existing in the protein molecule becomes 0.

Accordingly, it is very important to find a pI value by measuring the pH value that the net charge in the protein molecule becomes 0. The pH value plays a major role in understanding of a property of the protein molecule.

However, typical isoelectric point measuring methods such as an isoelectric focusing method and the like cannot effectively measure the isoelectric point of the bio molecule, cannot attain an accurate value, and have poor reproducibility. In addition, the typical isoelectric point measuring methods have some troubles measuring the isoelectric points of proteins having a high hydrophobic property, proteins having many basic groups, or proteins that are very big or small.

DISCLOSURE OF INVENTION

Technical Problem

The present invention provides a method for accurately measuring an isoelectric point using a field effect transistor (FET).

The present invention also provides a method for accurately measuring an isoelectric point using an FET.

Technical Solution

Other features will be apparent to those skilled in the art from the description and drawings, and from the claims.

The present invention provides a method for measuring an isoelectric point, the method including providing a field effect transistor including a substrate, source and drain electrodes disposed on the substrate and spaced apart from each other, and a channel region between the source and drain electrodes, providing a first electrolyte solution having a first concentration to the channel region of the field effect transistor and measuring a first current value of the channel region between the source and drain electrodes, providing a second electrolyte solution having a second concentration greater than the first concentration and measuring a second current value of the channel region between the source and drain electrodes, and determining the isoelectric point of the field effect transistor or a material disposed on the field effect transistor using a difference between the first and second current values.

Embodiments of the present invention also provide an apparatus for measuring an isoelectric point, the apparatus including a field effect transistor comprising a substrate, source and drain electrodes disposed on the substrate and spaced apart from each other, and a channel region between the source and drain electrodes, a first electrolyte solution supply unit for supplying a first electrolyte solution having a first concentration to the channel region, a second electrolyte solution supply unit for supplying a second electrolyte solution having a second concentration to the channel region, wherein the second electrolyte solution has a same pH as the first electrolyte solution and the first concentration is less than the second concentration, and a current measuring unit measuring a current flowing along the channel region when the first and second electrolyte solutions are supplied.

The details of one or more embodiments are set forth in the accompanying drawings and the description below

Advantageous Effects

According to a method for measuring an isoelectric point using an FET of the present invention, the isoelectric point of the bio molecule or material can be accurately measured by measuring hydrogen ion concentration of an electrolyte solution and a current variation of the FET in accordance with a variation of the ion concentration.

BRIEF DESCRIPTION OF THE DRAWINGS

The accompanying figures are included to provide a further understanding of the present invention, and are incorporated in and constitute a part of this specification. The drawings illustrate exemplary embodiments of the present invention and, together with the description, serve to explain principles of the present invention. In the figures.

MODE FOR THE INVENTION

Figure 1:
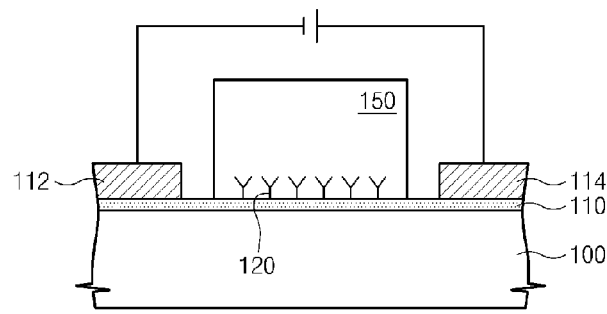
FIG. 1 is a cross-sectional view of a field effect transistor (FET) according to an embodiment of the present invention.

Preferred embodiments of the present invention will be described below in more detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Like reference numerals refer to like elements throughout.

In the following description, the technical terms are used only for explain a specific exemplary embodiment while not limiting the present invention. The terms of a singular form may include plural forms unless referred to the contrary. The meaning of "include", "comprise", "including", or "comprising" specifies a property, a region, a fixed number, a step, a process, an element and/or a component but does not exclude other properties, regions, fixed numbers, steps, processes, elements and/or components. It will be understood that when an element such as a layer, film, region, or substrate is referred to as being 'on' another element, it can be directly on the other element or intervening elements may also be present.

Additionally, the embodiment in the detailed description will be described with sectional views as ideal exemplary views of the present invention. In the figures, the dimensions of layers and regions are exaggerated for clarity of illustration. Accordingly, shapes of the exemplary views may be modified according to manufacturing techniques and/or allowable errors. Therefore, the embodiments of the present invention are not limited to the specific shape illustrated in the exemplary views, but may include other shapes that may be created according to manufacturing processes. Areas exemplified in the drawings have general properties, and are used to illustrate a specific shape of a semiconductor package region. Thus, this should not be construed as limited to the scope of the present invention.

Hereinafter, an exemplary embodiment of the present invention will be described with the accompanying drawings.

FIG. 1 is a cross-sectional view of a field effect transistor (FET) according to an embodiment of the present invention. The FET of this embodiment may be either a bio FET used for detecting a property of a bio molecule or a material FET used for detecting a property of a material.

Description will be exemplarily made on the FET formed with a silicon-on-insulator (SOI) substrate or a bulk semiconductor substrate having a multi-layer.

Referring to FIG. 1, the FET with the SOI substrate includes a support substrate 100, source and drain electrodes 112 and 114, and a channel region. In more detail, the FET includes the support substrate 100, a doping layer 110 of a predetermined conductive type disposed on a surface of the support substrate 100 and the source and drain electrodes 112 and 114 provided on opposite ends of the doping layer 110.

The support substrate 100 may be formed of silicon (Si), germanium (Ge), silicon-germanium (SiGe), an oxide-based material, a compound-based material, or carbon.

The doping layer 110 may be a diffusion layer formed through an impurity diffusion process, an ion implantation layer formed through an impurity ion implantation process, or an epitaxial layer formed through an epitaxial growth process.

The FET including a bulk semiconductor substrate having a multi-layer will be described in detail below Referring again to FIG. 1, the FET with the bulk semiconductor substrate includes a semiconductor substrate 100, source and drain electrodes 112 and 114, and a channel region. In more detail, the semiconductor substrate 100 is a first conductive type. A doping layer 110 of a second conductive type is disposed on a surface of the semiconductor substrate 100. The source and drain electrodes 112 and 113 are provided on opposite ends of the doping layer 110.

The semiconductor substrate 100 may be formed of silicon (Si), germanium (Ge), silicon-germanium (SiGe), an oxide-based material, a compound-based material, or carbon.

The doping layer 110 has a conductive type that is complementary to that of the semiconductor substrate 100. For example, when the semiconductor substrate 100 has an N-type, the doping layer 110 has a P-type.

In the embodiment of the present invention, an FET having the P-type doping layer 110 is exemplarily described.

The doping layer 110 may be a diffusion layer formed through an impurity diffusion process, an ion implantation layer formed through an impurity ion implantation process, or an epitaxial layer formed through an epitaxial growth process. The doping layer 110 may have a width of about 1 nm to about 3,000,000 nm, a length of about 1 µm to about 2,000 µm, and a thickness of about 1 nm to about 1000 nm.

An electrolyte solution 150 is provided on a surface of the doping layer 110. Bio molecules or material, i.e., target molecules 120 are fixed on the surface of the doping layer 110 in the electrolyte solution 150.

The source and drain electrodes 112 and 114 are spaced apart from each other and electrically connected to the opposite ends of the doping layer 110. When a voltage is applied to the source and drain electrodes 112 and 114, a channel is formed in the doping layer 110 between the source and drain electrodes 112 and 114

Meanwhile, the doping layer between the source and drain electrodes 112 and 114 may be surface-treated such that the bio molecules or material can be fixed. That is, a functional group that can represent the pI may be introduced on the treated surface of the doping layer 110. For example, a carboxyl group (—COOH), a thiol group (—SH), a hydroxyl group (—OH), a silane group, an amine group, or an epoxy group may be introduced on the treated surface of the doping layer 110.

The bio molecules or material, i.e., the target molecules or material 120 fixed on the surface of the doping layer 110 between the source and drain electrodes 112 and 114 may be, for example, proteins, nucleic acids, organic molecules, inorganic molecules, an oxide material, or a metal oxide material. The protein molecules may be bio molecules such antigens, antibodies, matrix proteins, enzymes, coenzymes, ligands, aptamers, and receptors. The nucleic acids may be DNA, RNA, PNA, LNA, or a combination thereof.

The target molecules or material 120 may be directly fixed on the doping layer 110 or indirectly fixed on the doping layer 110 by a medium between the doping layer 110 and the target molecules or material 120. The medium may be organic molecules, inorganic molecules, protein molecules, nucleic acids, or enzymes.

Although the doping layer 110 is provided on the support between the source and drain electrodes 112 and 114 or the surface of the semiconductor substrate 100, the present invention is not limited to these configurations. That is, a gate electrode may be provided on the substrate 100 between the surface and drain electrodes 112 and 114. In addition, the source and drain electrodes 112 and 114 may be a doping region formed by doping impurities into the substrate 100.

Figure 2:
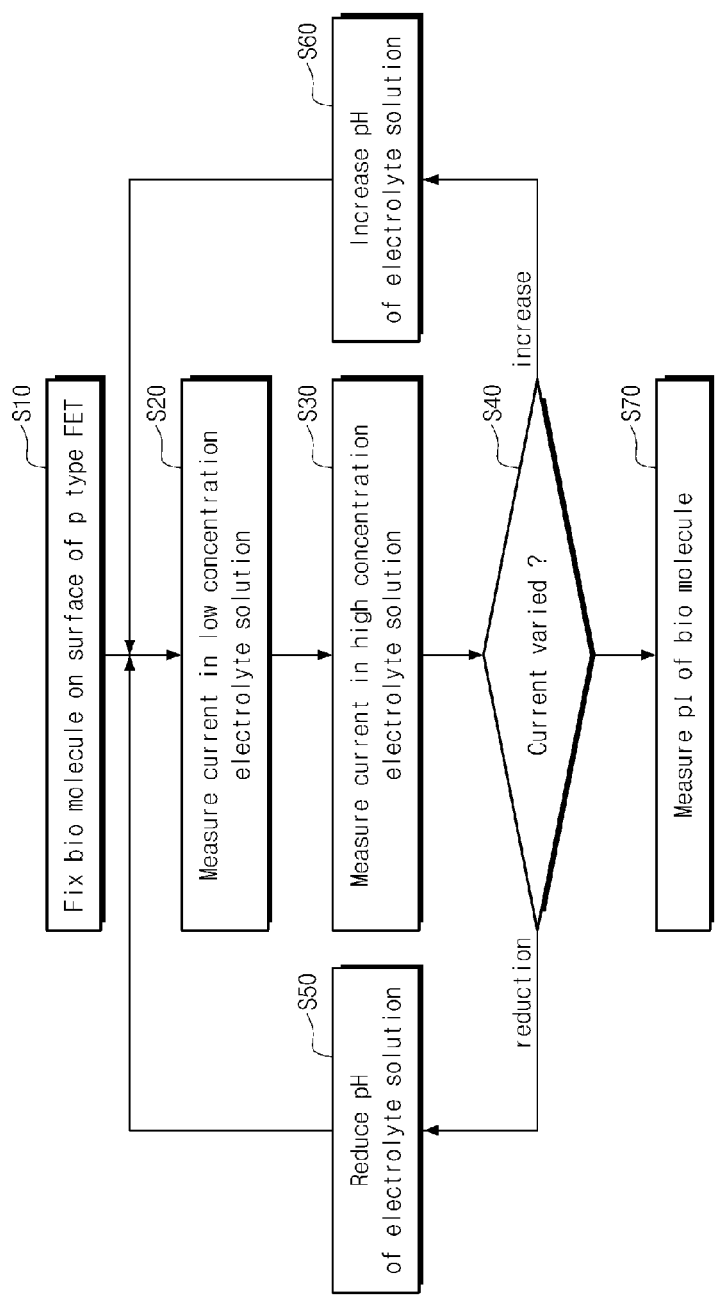
FIGS. 2 and 3 are flowcharts illustrating a method for measuring an isoelectric point using an FET according to an embodiment of the present invention.
Figure 3:
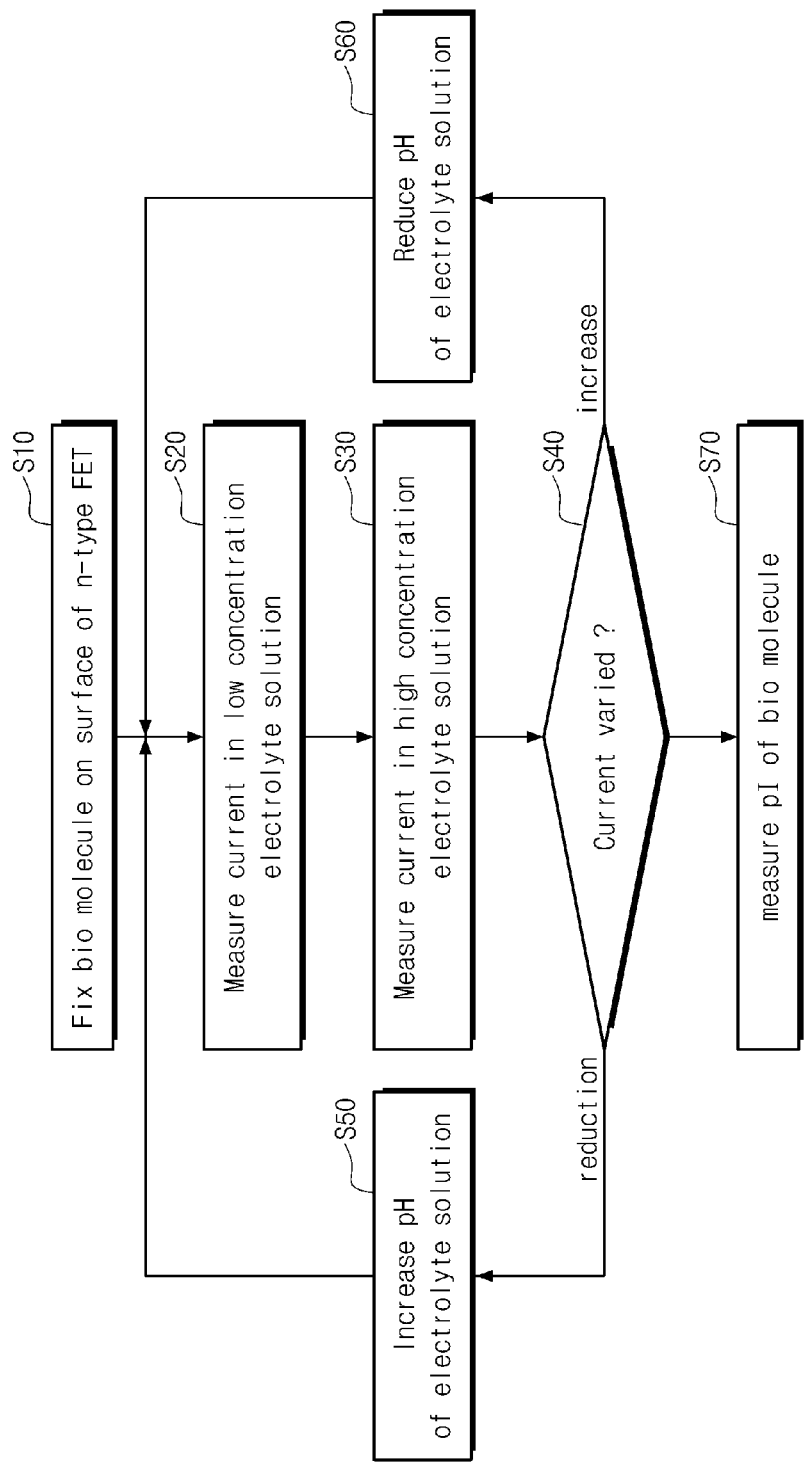

The following will describe a method for measuring a pI of a bio molecule or material according to an embodiment of the present invention with reference to FIGS. 2 and 3.

FIGS. 2 and 3 are flowcharts illustrating a method for measuring a pI of a bio molecule or material according to an embodiment of the present invention. In more detail, FIG. 2 is a flowchart illustrating a method for measuring a pI of a bio molecule or material using a P-type FET and FIG. 3 is a flowchart illustrating a method for measuring a pI of a bio molecule or material using a N-type FET.

According to an embodiment of the present invention, the pI of the bio molecule or material may be attained by measuring a variation of a current flowing along a channel region of the FET while varying pH or ion concentration of the electrolyte solution 150.

In a first process, the bio molecule or material is fixed on the surface of the doping layer 110 of the FET (S10). The bio molecule or material may be, for example, the target molecule or material 120.

In a second process, the electrolyte solution is provided on the doping layer 110 and a voltage is applied to the source and drain electrodes 112 and 114 to measure a current of the channel region (S20). Here, the measure current will be referred to as a first current value. The bio molecule or material may be positively or negatively charged in accordance with the pI.

Describing in more detail, when the voltage is applied to the source and drain electrodes 112 and 114, the current flows between the source and drain electrodes 112 and 114 through the channel region of the doping layer 110. Here, the value of the current flowing along the channel region may vary in accordance with a functional group on the surface of the doping layer 110. That is, the value of the current flowing of the channel region may vary depending on a charge quantity of the bio molecule, i.e., the target molecule 120, fixed on the surface of the doping layer 110.

That is, the target molecules 120 are fixed on the surface of the doping layer 110 while being positively or negatively charged. The value of the current flowing along the channel region may be increased or reduced depending on the charge quantity of the bio molecules. That is, for the P-type FET, the value of the current may vary depending on holes of the channel region in accordance with the charge quantity of the target molecules 120 fixed on the doping layer. For the N-type FET, the value of the current may vary depending on electrons of the channel region in accordance with the charge quantity of the target molecules 120 fixed on the doping layer.

Further, the value of the current flowing along the channel region may also vary depending on intensity of ions of the electrolyte solution 150 and hydrogen ion concentration (pH) of the electrolyte solution 150. In addition, when the pI of the bio molecule or material on the surface of the doping layer 110 is higher than the pH of the electrolyte solution, the bio molecule or material is fixed on the surface of the doping layer 110 while being positively charged. When the pI of the bio molecule or material on the surface of the doping layer 110 is lower than the pH of the electrolyte solution, the bio molecule or material is fixed on the surface of the doping layer 110 while being negatively charged.

In a third process, an electrolyte solution having the same pH as the electrolyte solution 150 of the second process and the lower concentration than the ion concentration of the electrolyte solution of the first process is provided and a current variation at the channel region is measured (S30). Alternatively, an electrolyte solution having the higher concentration than the ion concentration of the electrolyte solution 150 of the second process is provided and the current variation at the channel region may be measured (S30). Here, the measure current will be referred to as a second current value. The second current value will be increased or reduced to be greater or less than the first current value by a screening phenomenon of the charges in the electrolyte solution.

In the second and third processes, the bio molecule or material is fixed on the surface of the doping layer 110 while being negatively or positively charged and being shielded by the ions existing in the electrolyte solution 150.

Describing in more detail, the bio molecule fixed on the surface of the doping layer 110 and positively and negatively charged is surrounded by the ions existing in the electrolyte solution 150. Here, when the pI of the bio molecule or material is higher than the pH of the electrolyte solution 150, the bio molecule or material is positively charged. Therefore, the positive charges are screened by the ions of the electrolyte solution 150. On the other hand, when the pI of the bio molecule or material is lower than the pH of the electrolyte solution 150, the bio molecule or material is negatively charged. Therefore, the negative charges are screened by the ions of the electrolyte solution 150.

At this point, as the number of ions existing in the electrolyte solution 150 increases, the charges of the bio molecule or material are more strongly screened by the ions and thus the charges are shielded (through Debye shielding). Therefore, the affection of the charges of the bio molecule or material on the surface of the doping layer 110 is increasingly reduced. That is, a potential length (i.e., Debye length) at which the charges affect the surface of the doping layer 110 is reduced.

For example, when the bio molecule or material fixed on the doping layer 110 of the FET is negatively charged, the positive ions existing in the electrolyte solution 150 gradually surround the negative charges of the proteins and thus the charges are shielded. Therefore, the affection of the negative charges on the surface of the doping layer 110 is exponentially reduced.

That is, in the FET, the bio molecule or material fixed on the surface of the doping layer 110 varies the current value of the channel region depending on the ion concentration of the electrolyte solution 150.

Therefore, for the P-type FET, when the pI of the bio molecule or material is greater than pH of the electrolyte solution (pI>pH), the bio molecule or material is positively charged and fixed on the doping layer 110. Therefore, the holes may be depleted in the channel region. Here, as the ion concentration of the electrolyte solution increases, the negative ions of the electrolyte solution screen the positive charges of the bio molecule or material and thus the potential length (Debye length) at which the positive charges affect the doping layer 110 is reduced. Therefore, an amount of the current flowing along the channel region increases. On the other hand, as the ion concentration of the electrolyte solution is reduced, the potential length (Debye length) at which the positive charges affect the doping layer 110 increases. Therefore, an amount of the current flowing along the channel region is reduced.

On the other hand, for the P-type FET, when the pI of the bio molecule or material is less than pH of the electrolyte solution (pI<pH), the bio molecule or material is negatively charged and fixed on the doping layer 110. Therefore, the holes may be accumulated on the channel region. Here, as the ion concentration of the electrolyte solution increases, the positive ions of the electrolyte solution screen the negative charges of the bio molecule or material and thus the potential length (Debye length) at which the negative charges affect the doping layer 110 is reduced. Therefore, an amount of the current flowing along the channel region is reduced. On the contrary, as the ion concentration of the electrolyte solution is reduced, the potential length (Debye length) at which the negative charges affect the doping layer 110 increases. Therefore, an amount of the current flowing along the channel region increases.

Meanwhile, the current variation in the N-type FET is done on the contrary to the above.

As described above, in the solution having a specific pH, the range of the current variation depending on the ion concentration of the electrolyte solution is increasingly reduced as the pH of the electrolyte solution doses the pI of the bio molecule or material. Therefore, when the pH of the electrolyte solution is same as the pI of the bio molecule or material, the current value on the channel region may be constant regardless of the ion concentration.

Therefore, in a fourth process, a difference between the first current value in the second process and the second current valve in the third process is analyzed (S40). In accordance with the result of the fourth process, the pH of the electrolyte solution is varied, after which the second to fourth processes are repeated to detect the current variation while varying the ion concentration.

That is, for the P-type FET, when the ion concentration of the electrolyte solution is reduced and a difference ($\Delta I$) attained by subtracting the first current value from the second current value is negative or when the ion concentration of the electrolyte solution is increased and a difference ($\Delta I$) attained by subtracting the first current value from the second current value is positive, the positive charges of the bio molecule or material are screened by the negative ions and thus the pI of the bio molecule or material is greater than the pH of the electrolyte solution. Therefore, the difference between the pI of the bio molecule or material and the pH of the electrolyte solution is reduced by increasing the pH of the electrolyte solution (S50).

On the other hand, for the P-type FET, when the ion concentration of the electrolyte solution is reduced and a difference ($\Delta I$) attained by subtracting the first current value from the second current value is positive or when the ion concentration of the electrolyte solution is increased and a difference ($\Delta I$) attained by subtracting the first current value from the second current value is negative, the negative charges of the bio molecule or material are screened by the positive ions and thus the pI of the bio molecule or material is less than the pH of the electrolyte solution. Therefore, the difference between the pI of the bio molecule or material and the pH of the electrolyte solution is reduced by reducing the pH of the electrolyte solution (S60).

Meanwhile, when the difference between the first and second current values is 0 even if the ion concentration of the electrolyte solution varies, i.e., when there is no current variation even if the ion concentration of the electrolyte solution varies, the net charge value of the bio molecule or material becomes 0. Here, when the difference between the first and second current values becomes 0, this means a state where a current value difference between high and low concentrations cannot be detected in accordance with the resolution. Therefore, when the current variation between the high and lower concentrations is not detected, the pH of the electrolyte solution corresponds to the pI of the bio molecule or material and thus the pI of the bio molecule or material is measured (S70).

The above described method for measuring the pI of the bio molecule or material can be identically applied to the N-type FET.

That is, for the N-type FET, when the ion concentration of the electrolyte solution is reduced and a difference ($\Delta I$) attained by subtracting the second current value from the first current value is negative or when the ion concentration of the electrolyte solution is increased and a difference ($\Delta I$) attained by subtracting the second current value from the first current value is positive, the difference between the pI of the bio molecule or material and the pH of the electrolyte solution is reduced by reducing the pH of the electrolyte solution.

On the other hand, for the P-type FET, when the ion concentration of the electrolyte solution is reduced and a difference ($\Delta I$) attained by subtracting the second current value from the first current value is positive or when the ion concentration of the electrolyte solution is increased and a difference ($\Delta I$) attained by subtracting the second current value from the first current value is negative, the difference between the pI of the bio molecule or material and the pH of the electrolyte solution is reduced by increasing the pH of the electrolyte solution.

Figure 4:
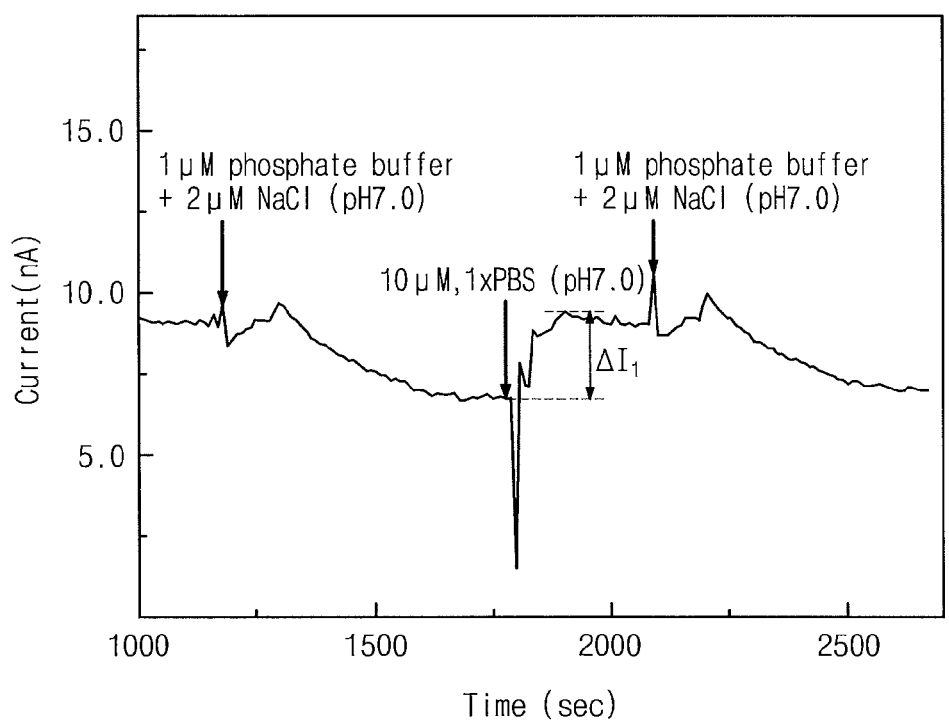
FIGS. 4 and 5 are graphs illustrating a current flowing along a channel region of an FET and measured while varying a pH and ion concentration of an electrolyte concentration.
Figure 5:
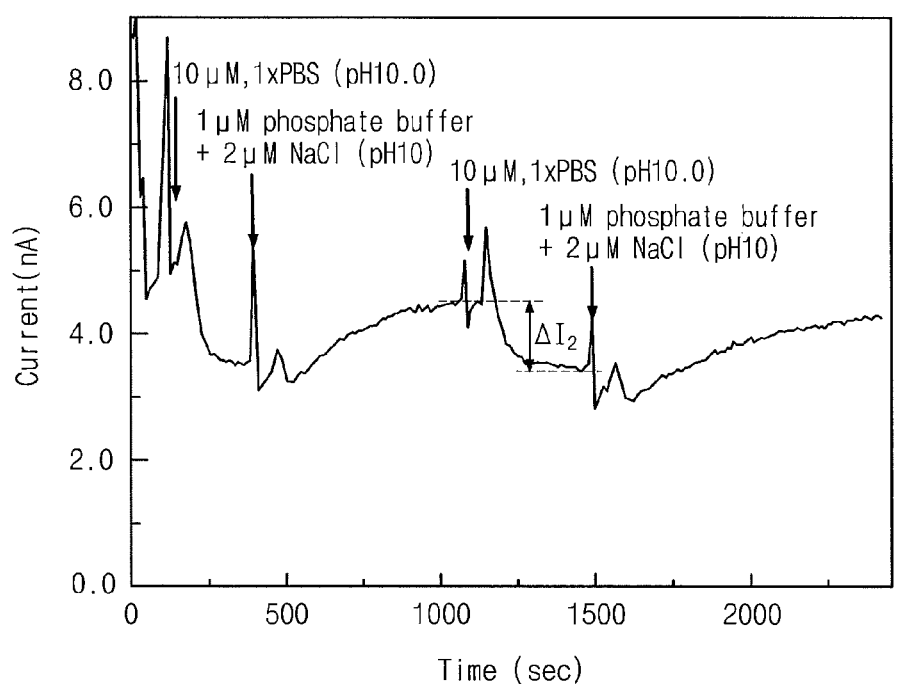

Test data for measuring the pI of the bio molecule or material using the abovedescribed method for measuring the pI of the bio molecule or material are shown in FIGS. 4 and 5. That is, FIGS. 4 and 5 illustrate current variations depending on variations of the pH of the electrolyte solution and the ion concentration.

The P-type FET is used, and an anti-PSA (prostate specific antigen) are used as the bio molecules. An electrolyte solution of 10 µM phosphate buffered saline (PBS) solution (pH 7.0) and 10 µM PBS solution (pH 10.0) is prepared. A low concentration ion solution of 1 µM phosphate buffer solution containing 2 µM NaCl NaC1 solution (pH 7.0) and 1 µM phosphate buffer solution containing 2 µM NaCl (pH 10) is prepared.

FIG. 4 illustrates current variations depending on an ion concentration of the solutions (pH 7.0). Referring to FIG. 4, when the low or high concentration solution is injected, the solution is stabilized after a predetermined time has elapsed. That is, it can be noted that, when the low concentration solution is injected, the current is gradually reduced and then stabilized. It can be further noted that, when the high concentration solution is injected, the current is progressively increased and then stabilized.

That is, it can be noted that the current when the high concentration solution is injected is higher than the current when the low concentration solution is injected ($\Delta I_1 > 0$). This means that the positive charges of the anti-PSA are gradually screened by the negative ions of the electrolyte solution and thus the current increases. On the contrary, it can be noted that, when the low concentration ion solution is injected, the opposite phenomenon to the above occurs. Accordingly, it can be noted that the anti-PSA has a pI greater than the pH 7.0.

FIG. 5 illustrates current variations depending on an ion concentration of the solutions (pH 10). Referring to FIG. 5, it can be noted that, when the low or high concentration solution is injected, the current is progressively increased and then stabilized. It can be further noted that, when the high concentration solution is injected, the current is progressively reduced and then stabilized.

That is, it can be noted that the current when the high concentration solution is injected is less than the current when the low concentration solution is injected ($\Delta I_2 < 0$). This means that the negative charges of the anti-PSA are gradually screened by the positive ions of the electrolyte solution and thus the current is reduced. On the contrary, it can be noted that, when the low concentration ion solution is injected, the opposite phenomenon to the above occurs. Accordingly, it can be noted that the anti-PSA has a pI less than the pH 10.

According to the test data of FIGS. 3A and 3B, it can be observed that the anti-PSA has the PI grater than pH 7.0 but less than pH 10.

After the above, the current variation depending on the ion concentration is repeatedly measured while adjusting the pH of the electrolyte solution within a range a value greater than pH 7.0 to a value less than pH 10. As a result, the pI of the anti-PSA can be more accurately measured.

Figure 6:
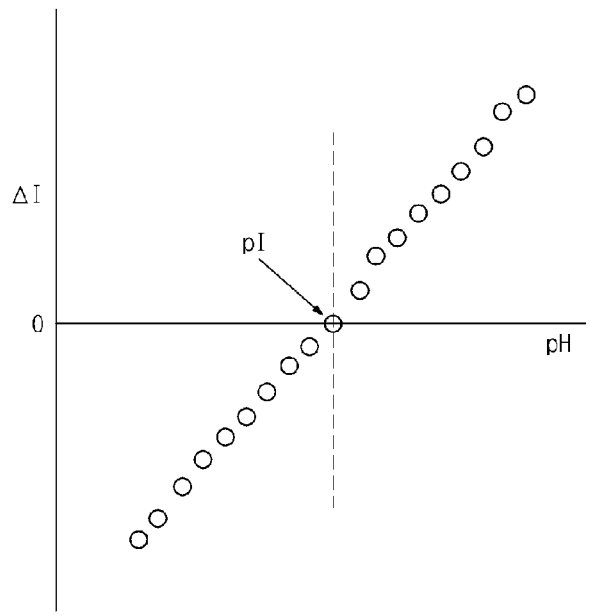
FIG. 6 is a graph illustrating a current difference between buffer solutions having different ion concentrations for each pH of an electrolyte solution.

That is, as shown in a graph of FIG. 6, the pI of the bio molecule or material can be measured by finding a point where a current difference between the high and low concentrations becomes 0. FIG. 6 is a graph illustrating a current difference between two buffer solutions having different ion concentrations depending on the pH of the electrolyte solution.

In FIG. 6, an X-axis indicates the pH of the electrolyte solution and a Y-axis denotes the current difference ($\Delta I$) between the high and low concentration solutions. Referring to FIG. 6, when the current difference ($\Delta I$) between the high and low concentration solutions is measured while adjusting the pH, the current difference ($\Delta I$) is gradually reduced to 0 as the pH gradually doses the pI of the bio molecule or material. That is, the X-axis coordinate at the point where the current difference ($\Delta I$) becomes 0 becomes the pI of the bio molecule or material. This relationship can be expressed by the following polynomial.

$y = a_1 x^n + a_2 x^{n-1} + a_3 x^{n-2} + + a_{n-1} x^2 + a_n x^1$ (where, y is the current different and x is the pH of the electrolyte solution)

Meanwhile, a pI of the surface of the channel region of the FET can be measured using the method for measuring the pI of the bio molecule or material according to the embodiment.

Figure 7:
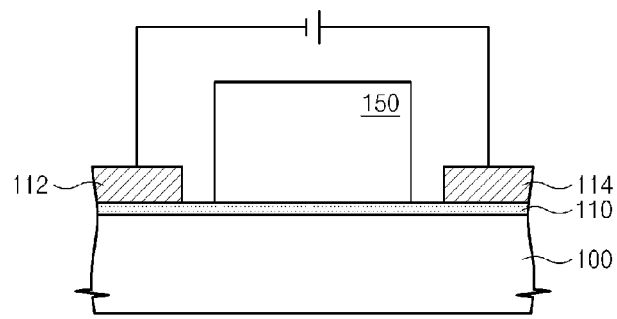
FIG. 7 illustrates cross-sectional views of an FET used for measuring an isoelectric point according to an embodiment of the present invention.

FIG. 7 illustrates a cross-sectional view of an FET to which the method for measuring the pI of the bio molecule or material according to the embodiment is applied.

Referring to FIG. 7, a pI of the surface of the channel region of the FET can be measured using the method for measuring the pI of the bio molecule or material according to the embodiment. That is, an FET including a support or semiconductor substrate 100, a doping layer 110, and source and drain electrodes 112 and 114 are prepared. An electrolyte solution 150 is applied on the surface of the doping layer 110 between the source and drain electrodes 112 and 114

Next, a voltage is applied to the source and drain electrodes 112 and 114 and a current value of a channel region on the doping layer 110, after which the current variation of the channel region is measured while varying the ion concentration and pH of the electrolyte solution 150. The pI of the surface of the doping layer 110 may be measured when there is no current variation depending on the variations of the ion concentration and pH of the electrolyte solution 150.

Meanwhile, the pI of the surface of the channel region of the FET may be measured after a functional group (e.g., hydroxyl group (—OH)) representing the p1 is introduced on the surface of the doping layer 110 by surface-treating the doping layer 110.

Figure 8:
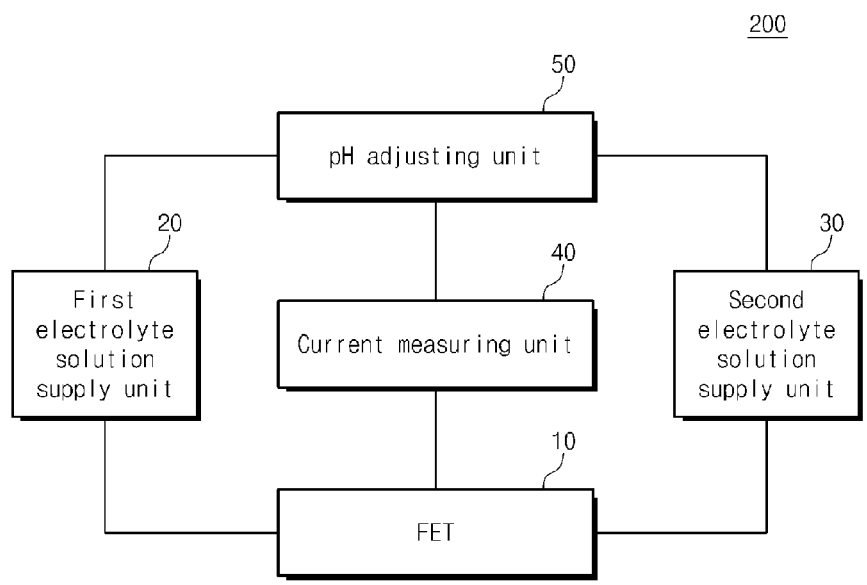
FIG. 8 is a schematic diagram of an apparatus for measuring an isoelectric point according to an embodiment of the present invention.

FIG. 8 is a schematic view of an apparatus for measuring a pI of a material according to an embodiment of the present invention.

Referring to FIG. 8, an apparatus 200 for measuring a pI of a material according to an embodiment of the present invention includes an FET 10, a first electrolyte solution supply unit 20 supplying a first electrolyte solution having a first concentration, a second electrolyte solution supply unit 30 supplying a second electrolyte solution having a second concentration, a current measuring unit 40, and a pH adjusting unit 50.

The FET 10 is used for measuring the pI of a bio molecule or material, including a substrate, source and drain electrodes spaced apart from each other on the substrate, and a channel region between the source and drain electrodes. A bio molecule or material whose pI will be measured is fixed on the channel region of the FET 10. Since the FET 10 is already described with reference to FIG. 1, a detailed description will be omitted in this embodiment.

In order to measure the pI of the bio molecule or material, the FET 10 is connected to the first and second electrolyte solution supply units 20 and 30.

The first and second electrolyte solution supply units 20 and 30 store different electrolyte solutions. That is, the first and second electrolyte solution supply units 20 and 30 store low and high concentration electrolyte solutions, respectively. In order to measure the pI of the bio molecule or material fixed on the channel region of the FET 10 or the pI of the FET, the first and second electrolyte solution supply units 20 and 30 alternately supplies first and second electrolyte solutions respectively having first and second concentrations. At this point, the first electrolyte solution has the same pH as the second electrolyte solution.

The current measuring unit 40 is connected to the FET 10 to measure a current variation of the channel region. That is, the current measuring unit 40 can measure the current value of the channel region when the first and second electrolyte solutions are supplied. The current value of the channel region varies depending on a charge quantity of the bio molecule or material, an ion concentration of the electrolyte solution supplied to the channel region, and a pH of the electrolyte solution.

That is, the current measuring unit 40 measures the current variation of the channel region of the FET 10 after the low concentration electrolyte solution is supplied. Next, the current variation of the channel region of the FET is measured after the high concentration electrolyte solution is supplied. Subsequently, a difference between the current variations measured when the low and high concentrations are supplied is calculated. At this point, when the difference between the current variations is 0, the pH of the low and high concentration electrolyte solutions becomes the pI of the material fixed on the channel region. That is, the current measuring unit 40 can measure the pI of the material by calculating the difference between the current variations.

The pH adjusting unit 50 adjusts pH of the electrolyte solutions stored in the first and second electrolyte solution supply units 20 and 30 in accordance with the current value measured by the current measuring unit 40. That is, the pH adjusting unit 50 increases or decreases the pH of the electrolyte solution in accordance with the difference between the current variations measured when the low and high concentrations are supplied. When the difference between the current variations is 0, it is not necessary to adjust the pH of the first and second electrolyte solutions.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

The invention claimed is:

1. A method for measuring an isoelectric point, comprising:
   providing a field effect transistor comprising a substrate, source and drain electrodes disposed on the substrate and spaced apart from each other, and a channel region between the source and drain electrodes;
   providing a first electrolyte solution having a first concentration to the channel region of the field effect transistor and measuring a first current value of the channel region between the source and drain electrodes;
   providing a second electrolyte solution having a second concentration greater than the first concentration and measuring a second current value of the channel region between the source and drain electrodes; and
   determining the isoelectric points of the field effect transistor or materials disposed on the field effect transistor using a difference between the first and second current values.

2. The method of claim 1, wherein the first electrolyte solution has a same pH with the second electrolyte solution.

3. The method of claim 2, wherein the isoelectric point is a pH of the electrolyte solutions when the difference between the first and second current values becomes 0.

4. The method of claim 1, further comprising varying a pH of each of the first and second electrolyte solutions according to a result of the difference between the first and second current values.

5. The method of claim 4, wherein the measuring of the first and second current values, the determining of the isoelectric point of the field effect transistor or the material disposed on the field effect transistor, the varying of the pH of the electrolyte solution are repeated until the difference between the first and second current values becomes 0 where the pH of the electrolyte solution can be determined.

6. The method of claim 4, wherein the field effect transistor is one of P-type and N-type field effect transistors.

7. The method of claim 6, wherein the varying of the pH of the electrolyte solution comprises reducing the pH of the electrolyte solution when the field effect transistor is the P-type field effect transistor and the second current value is less than the first current value.

8. The method of claim 6, wherein the varying of the pH of the electrolyte solution comprises increasing the pH of the electrolyte solution when the field effect transistor is the P-type field effect transistor and the second current value is greater than the first current value.

9. The method of claim 6, wherein the varying of the pH of the electrolyte solution comprises increasing the pH of the electrolyte solution when the field effect transistor is the N-type field effect transistor and the second current value is less than the first current value.

10. The method of claim 6, wherein the varying of the pH of the electrolyte solution comprises reducing the pH of the electrolyte solution when the field effect transistor is the N-type field effect transistor and the second current value is greater than the first current value.

11. The method of claim 1, further comprising fixing a biomolecule or other molecule on the channel region of the field effect transistor after the field effect transistor is provided.

12. The method of claim 11, wherein the biomolecule is selected from the group consisting of a protein, a nucleic acid, an organic molecule, and an inorganic molecule.

13. The method of claim 12, wherein the nucleic acid is selected from the group consisting of DNA, RNA, PNA, LNA, and a combination thereof.

14. The method of claim 12, wherein the protein is selected from the group consisting of an enzyme, a matrix protein, an antigen, an antibody, a ligand, an aptamer, and a receptor.

15. The method of claim 11, further comprising forming a functional group representing the isoelectric point on a surface of the channel region before the biomolecule is fixed.

16. The method of claim 1, wherein the field effect transistor further comprises a doping layer, which is doped with an opposite conductive material to the substrate, in the channel region.

17. The method of claim 1, wherein the FET comprises a semiconductor oxide or metal oxide ceramic and the determining of the isoelectric point comprises an isoelectric point of the semiconductor oxide or metal oxide ceramic.

18. An apparatus for measuring an isoelectric point, comprising:
   a field effect transistor comprising a substrate, source and drain electrodes disposed on the substrate and spaced apart from each other, and a channel region between the source and drain electrodes;
   a first electrolyte solution supply unit for supplying a first electrolyte solution having a first concentration to the channel region;
   a second electrolyte solution supply unit for supplying a second electrolyte solution having a second concentration to the channel region, wherein the second electrolyte solution has a same pH as the first electrolyte solution and the first concentration is less than the second concentration; and
   a current measuring unit measuring a first current value and a second current value flowing along the channel region when the first and second electrolyte solutions are supplied, respectively;
   wherein the apparatus is configured to determine the isoelectric points of the FET or materials disposed on the FET using a difference between the first current value and the second current value of the current measuring unit.

19. The apparatus of claim 18, further comprises a controller that adjusts the pH of the first and second electrolyte solutions depending on a current variation of the channel region when the first and second electrolyte solutions are supplied.

20. The apparatus of claim 18, wherein the isoelectric point is determined when the difference between current values becomes 0, the current values are measured by the current measuring unit when the first and second electrolyte solutions are each supplied on the channel region.

* * * * *